United States Patent [19]

Weilbacher et al.

[11] Patent Number: 4,460,354
[45] Date of Patent: Jul. 17, 1984

[54] CLOSED WOUND SUCTION EVACUATOR

[75] Inventors: Eugene E. Weilbacher; Dean A. Ransom, both of New Philadelphia, Ohio

[73] Assignee: Snyder Laboratories, Inc., Dover, Ohio

[21] Appl. No.: 166,940

[22] Filed: Jul. 8, 1980

[51] Int. Cl.³ .............................................. A61M 1/06
[52] U.S. Cl. ..................................... 604/73; 604/131; 604/181
[58] Field of Search ................................ 604/212–216, 604/218, 134, 146, 73, 74, 131, 181; 222/214, 341; 92/43, 40; 141/26, 27; 417/472; 433/92; 267/164, 165, 64.23

[56] References Cited

U.S. PATENT DOCUMENTS

| | | | |
|---|---|---|---|
| 3,084,691 | 4/1963 | Stoner | 604/134 |
| 3,115,138 | 12/1963 | McElvenny et al. | 128/278 |
| 3,181,529 | 5/1965 | Wilburn | 128/2 |
| 3,376,868 | 4/1968 | Mondiadis | 128/278 |
| 3,513,829 | 5/1970 | Deuschle | 128/2 |
| 3,742,952 | 7/1973 | Magevs et al. | 128/278 |
| 3,774,611 | 11/1973 | Tussey et al. | 128/278 |
| 3,779,243 | 12/1973 | Tussey et al. | 128/278 |
| 3,809,086 | 5/1974 | Schachet | 128/278 |
| 3,875,941 | 4/1975 | Adair | 128/278 |
| 3,900,029 | 8/1975 | Melnick et al. | 128/278 |
| 3,946,739 | 3/1976 | Berman et al. | 128/304 |
| 4,022,209 | 5/1977 | Nehring | 128/278 |
| 4,063,556 | 12/1977 | Thomas et al. | 128/276 |
| 4,141,361 | 2/1979 | Snyder | 128/278 |
| 4,161,179 | 7/1979 | Abramson | 128/278 |
| 4,252,302 | 2/1981 | Musgrave | 267/165 |
| 4,278,089 | 7/1981 | Hock et al. | 128/278 |

FOREIGN PATENT DOCUMENTS

| | | | |
|---|---|---|---|
| 11884 | 4/1934 | Australia | 222/214 |
| 48164 | 3/1982 | European Pat. Off. | |

Primary Examiner—C. Fred Rosenbaum
Assistant Examiner—J. L. Kruter
Attorney, Agent, or Firm—Margaret L. Geringer; Richard H. Brink

[57] ABSTRACT

An evacuator system comprising a compressible container inside of which is positioned a vacuum assist device. The vacuum assist device aids in the expansion of the container and in developing a vacuum in the container upon expansion. The vacuum assist device within the evacuator acts to maintain a substantially constant level of vacuum as the evacuator expands while drawing fluids from a closed wound and collecting the fluids in the evacuator container. The evacuator includes an outlet for providing communication between the interior of the container and the atmosphere, and an inlet providing communication between the interior of the container and a drainage tube. The evacuator may include a novel valve mechanism which enables the evacuator to be activated, held in an activated position until needed, and then released from the held position for use to draw fluid from a patient.

15 Claims, 14 Drawing Figures

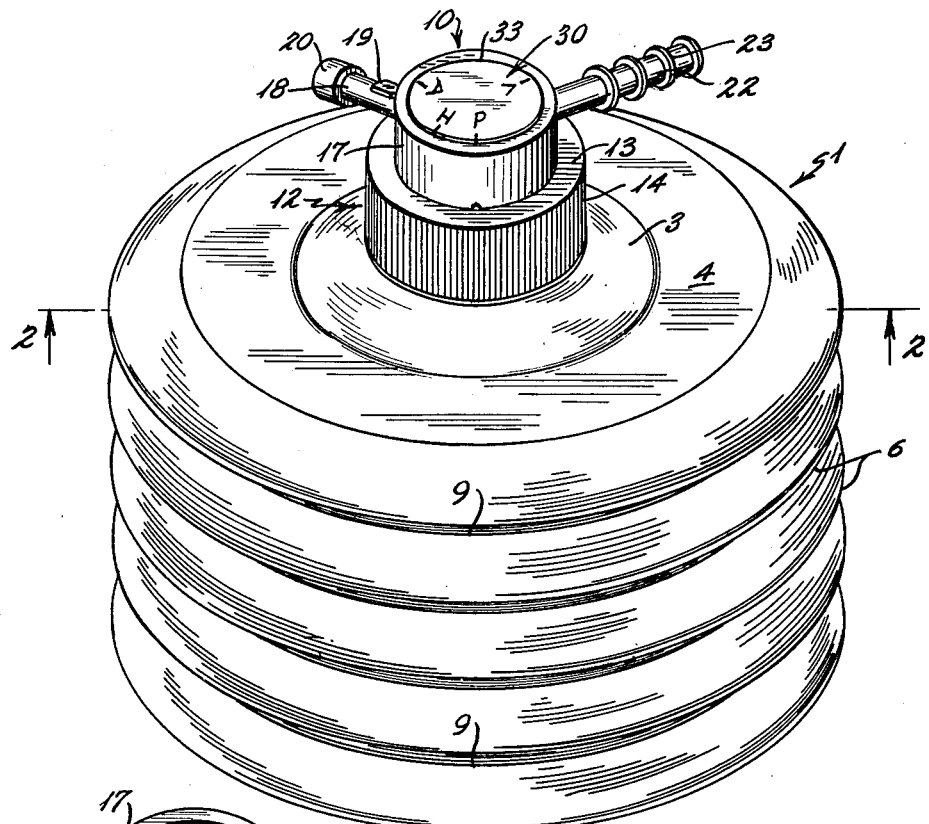
Fig.1
Fig.4
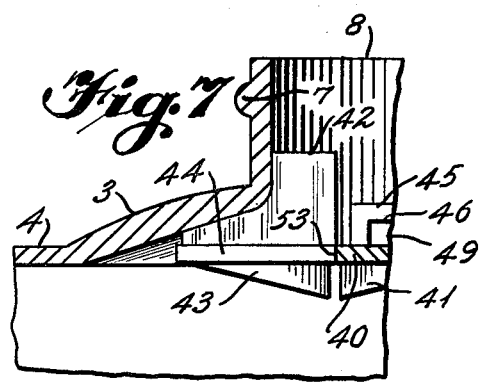
Fig.7

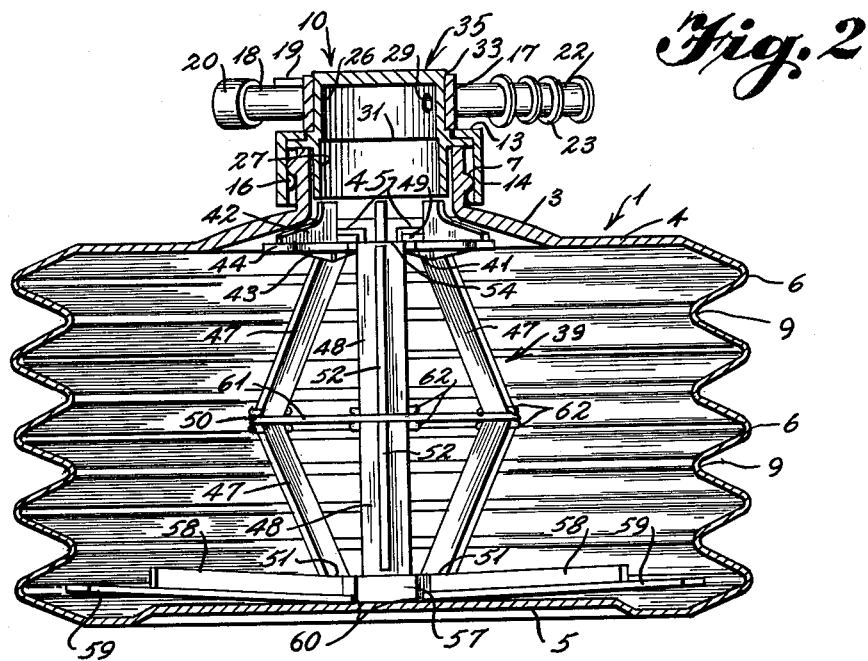
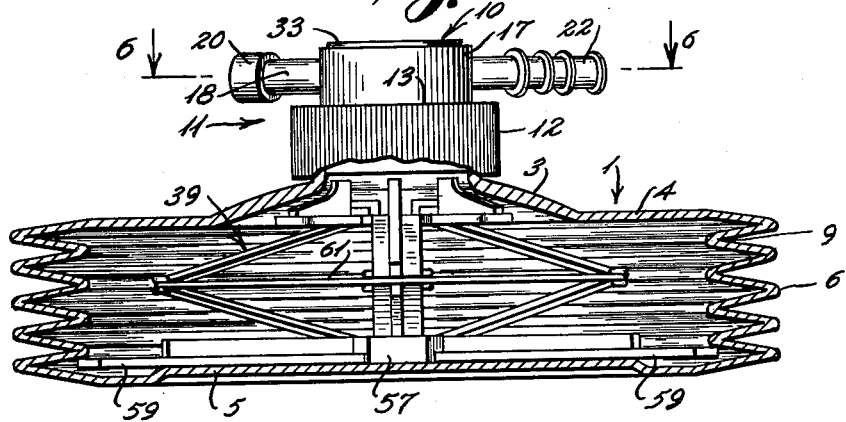
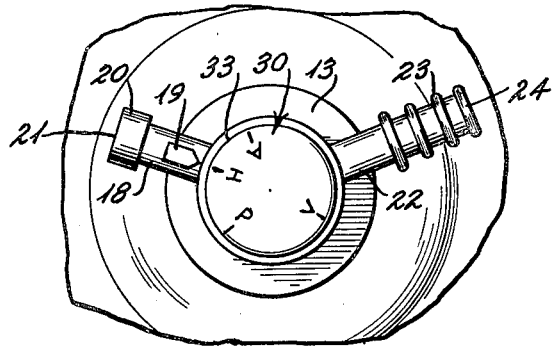
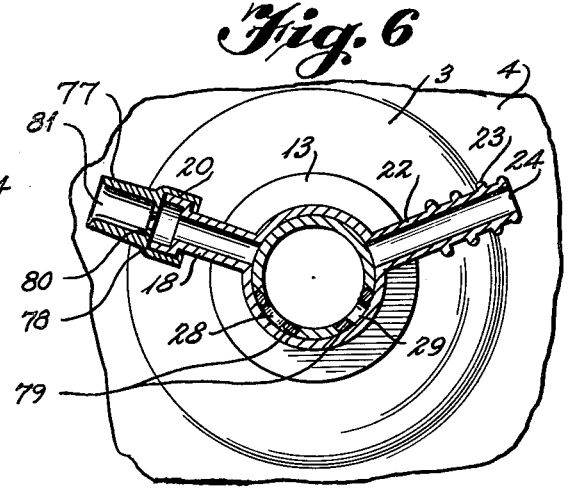

CLOSED WOUND SUCTION EVACUATOR

Background of the Invention

Evacuator systems comprising a flexible container to create a vacuum have been used in the drainage of fluids from the human body. One such prior art container is a bellows container which is compressible and resiliently expandable upon release of manually applied pressure, whereby a negative pressure or vacuum of predetermined magnitude is obtained within the container and can be applied to tubing or the like to which the container is connected. The containers are connected to tubing, preferably plastic, of suitable diameter and length, which tubing is connected to one or more lengths of plastic wound tubing, preferably of smaller diameter and of a type and kind compatible with human body tissue. The smaller wound tubing is laid within the wound of a patient for post-operative drainage of the wound. The wound tubing is provided with a multiplicity of small openings of suitable size and in predetermined space relation, whereby upon the application of negative pressure from the bellows container to the tubing, fluids are withdrawn from the wound and the adjacent tissue area into the tubing, and from the tubing into the container to aid in closing the wound and in removing unwanted fluid, to promote the healing process. The drainage of the wound is generally continued for a sufficient period of time to dry the wound.

The prior art evacuator containers were further provided with an outlet or vent opening, arranged to be selectively opened or closed by a manually operated valve to, during activation of the container, vent the gases in the container. The evacuator container could be further provided with support straps, or the like, whereby the container could be conveniently supported upon a support adjacent to the patient and/or could be carried by the body of the patient.

Another prior art evacuator is described in U.S. Pat. No. 3,115,138. Instead of a bellows container, the evacuator of this patent utilizes a self-contained compressible container including a plurality of springs disposed between the top and bottom of the container, with the opposite ends of each spring engaging the top and bottom, respectively, to exert a separating force thereon. The springs act in a similar manner to the compressible and resiliently expandable walls of the bellows, such that the springs within the compressible container are adapted to be compressed and to expand to develop a vacuum on expansion. This type of container also includes an appropriate means of communication between the interior of the container and the atmosphere and a means providing communication between the interior of the container and a drainage tube.

The prior art compressible evacuators, however, have several shortcomings in meeting the patient's needs. This type of container tends to experience substantial rapid decrease from maximum negative pressure to a minimum negative pressure during the expansion of the container from the compressed to the normal rest position. They also cannot be stored in the activated position.

OBJECTS OF THE INVENTION

An object of the present invention is to provide an improved suction evacuator system.

Another object of the invention is to provide a suction evacuator for draining fluids from the body into a compressible container.

Another object of the invention is to provide a suction evacuator utilizing a compressible container and a vacuum assist means to maintain a constant level of vacuum during the draw of the evacuator.

Another object of the invention is to provide a suction evacuator utilizing a compressible container and a vacuum assist means at an economical cost.

Another object of the invention is to provide a suction evacuator utilizing a compressible container and a vacuum assist means which is of simplified construction, which may be readily and economically manufactured at a low cost, and which will provide a uniform and reliable vacuum level during its use.

Another object of the present invention is to provide a closed wound suction evacuator system comprising a compressible container, a vacuum assist means and a valve means which cooperate for a simple, economic method of draining fluids from a closed wound in a post-operative procedure and which maintain a relatively uniform level of vacuum while draining fluids from the wound.

Another object of the present invention is to provide a closed wound suction evacuator system including a valve means which provides for the evacuator to be activated, held in activated position until needed, and then used to draw fluid from a patient.

SUMMARY OF THE INVENTION

In accordance with the present invention, an improved surgical evacuator system is provided to induce suction in drainage tubes used in draining a wound and to provide a container in which the withdrawn fluid may be collected. Important features of the improved evacuator system include a closed compressible container having top and bottom portions connected by a flexible sidewall. The container is adapted to be compressed and to expand to develop a vacuum on expansion. A novel vacuum assist means is disposed within the container to assist in the expansion of the container and in developing the vacuum in the container. The evacuator further includes an outlet means providing communication between the interior of the container and the atmosphere and an inlet means providing communication between the interior of the container and a drainage tube. The vacuum assist means is comprised of a spider device having two or more rib member means disposed between the top and bottom portions; a positioning means to securely locate the rib member means within the container; a hinge means to allow the rib member means to move from an extended rest position to a compressed activated postion; and a separate mechanical force means engaging exteriorly on the rib member means, which mechanical force means acts in a direction substantially perpendicular to the flexible sidewall to return the rib member means to their extended rest position. When it is stated that the force generating means engages exteriorly on the rib member means, this means or clarifies that the force means acts on the rib member means and is separate from the rib member means. The improved wound evacuator system by combining the vacuum developed by the expansion of the compressible container, such as a bellows container, with the vacuum developed by the expansion of the vacuum assist means develops and maintains a nearly uniform vacuum during the useful draw of the evacuator system. The improved wound evacuator may also utilize a novel valve means.

The improved suction evacuator system of the present invention will be described with reference to a particularly advantageous embodiment of the invention utilizing a bellows container. This embodiment is comprised of a bellows container inside of which is positioned a vacuum assist means and on top of which is a valve means retained by a screw on cap. The bellows container consists of a light-weight elastomeric plastic material which has a memory such that when the bellows are compressed from a normal rest position and then released a vacuum is developed within the container as the bellows return to the normal rest position. This vacuum in combination with the vacuum created by the vacuum assist means is used to draw fluids from the body into the container.

The amount of negative pressure in the container is directly related to the extent the container is compressed. That is, the more compressed, the greater the negative pressure. When the pressure is released and the bellows container returns to its normal position, the negative pressure developed by the bellows container decreases from a maximum to a minimum.

The vacuum assist means is positioned inside the bellows container in a normal expanded shape. The vacuum assist means may include a hinged spider device, while the separate mechanical force means may be an elastomeric ring. When the bellows container is compressed, the spider device is also compressed. The vacuum assist means utilizes the elastomeric ring which is stretched during the compression to return the spider device from its compressed position to its normal expanded shape. The further the spider device is compressed the smaller the required force to hold it down. This reduction in force is due to the changing angle the force of the elastic ring applies to resist the compression of the spider device. When downward pressure on the bellows container is released, the elastic ring applies a force which acts to return the spider device to its normal expanded shape.

Thus, when the bellows container and vacuum assist means are fully compressed, only a small amount of force is being applied by the vacuum assist means to push the bellows container back to its normal rest position, but as the bellows container moves towards its normal rest position, an increasingly greater force is applied by the vacuum assist means to expand the bellows container. The greater force applied by the vacuum assist means toward the end of its expansion relates to an increase in the amount of vacuum developed by the vacuum assist means as the spider device returns to its fully expanded shape. Thus, in the bellows container, as the vacuum developed by the bellows container decreases with outward movement, the vacuum developed by the vacuum assist means increases with outward movement. The net result is a relative level amount of vacuum developed during the useful draw of the bellows container.

The novel valve means allows the evacuator to be activated, held in an activated position until needed, and then used to draw fluids from a patient. The valve means has an indicator and four operative positions: activate (A), hold (H), patient (P), and wall suction (V), which are indicated on the top portion of the valve. The patient (P) position is aligned with an inlet orifice in the valve turret and the wall suction (V) position is aligned with vent orifice in the valve turret. With the valve indicator in the activate (A) position, on compression of the bellows container and the vacuum assist means, air is expelled and vented from the container through the wall suction (V) outlet orifice. While the bellows container and the valve assist means are in the compressed position, the valve indicator is rotated from the activate (A) to the hold (H) position. With the valve indicator in the hold (H) position, the vent orifice [wall suction (V)] and the inlet orifice [patient (P)] are both closed off sealing the bellows container, and there is no communication between the inside of the bellows container and the outside of the bellows container. The suction evacuator system can be stored in this condition until ready for use.

The suction evacuator system, with the valve indicator in the hold (H) position, is available for use. When needed, one end of suitable wound drainage tubing is attached to the inlet nipple on the valve cap and the other end is attached to a patient's wound. The valve indicator is turned to the patient (P) position, and a uniform level of vacuum applied to the patient's wound via the connecting drain tube. With the drain tube connected to a patient's wound, the above procedure can be repeated several times, if necessary, until the bellows container is full of drainage fluid after which the valve indicator can be put in the hold (H) position and the bellows container disconnected from the drainage tube and the patient.

If desired, the valve indicator can be put into the wall suction (V) position and a tube connected to wall suction via the vent nipple, which allows communication between drainage tube, the bellows container, and wall suction. In this mode, suction can be provided by an outside means and the drainage fluid collected in the bellows container. An advantage of the wall suction position in the removable cap is that this allows the complete cap and valve means with the attached tubing to the patient to be removed and attached to a rigid container for the wall suction mode without disturbing the patient, should this be desirable.

The present invention provides numerous advantages over the presently available closed wound suction evacuator systems. The present invention provides a means which a wound suction evacuator system can develop nearly constant vacuum during its draw cycle, can be stored in the activated state, is easily operated, and is small and light in weight.

It can be seen by the above description that a relatively low cost and reliable wound suction evacuator system is provided. The bellows container is cup-shaped, may be formed by relatively simple inexpensive molding techniques, and the entire structure can be made from relatively small number of parts, which may be easily fabricated and assembled.

The bellows container may be fabricated of relatively inexpensive plastic materials. The vacuum assist means spider device may be fabricated from a single molded piece of plastic, preferably polypropylene, and easily assembled to form the spider device insert, although the spider device may be fabricated from other materials and does not have to be fabricated in one piece. The elastic ring can be made from a rubber material and made to provide uniform and predictable action in returning the spider device to its expanded shape. Natural rubber is especially good as it has the best strength and return characteristics of the rubbers. Thus, the rubber ring which is relied upon to control in part the accuracy of the applied negative pressure, may be accurately fabricated and at relatively low cost.

The same effect that the elastic band has as a force generating member or mechanical force means may also be accomplished by connecting the legs of spider device 5 with springs or any material that is stretchable or resilient with good return characteristics. When the bellows is compressed, this compresses the spider device and causes the springs to be stretched. When the downward pressure on the container is released, the springs apply a force which acts to return the spider device to its normal expanded shape.

BRIEF DESCRIPTION OF THE DRAWINGS

In the drawings wherein like reference numerals refer to like parts throughout,

FIG. 1 is a perspective view of a closed wound suction evacuator system showing the bellows container and the valve means retained by a screwed on cap constructed in accordance with the present invention.

FIG. 2 of the drawings is a vertical section taken through the center of the evacuator along line 2—2 of FIG. 1 showing the valve means, bellows container in the normal rest position and the vacuum assist means in its normal expanded shape.

FIG. 3 of the drawings shows a side plane view of the valve means and a vertical section taken through the center of the bellows container along line 2—2 of FIG. 1 illustrating the bellows container and the vacuum assist means in the compressed position.

FIG. 4 is an expanded, detailed perspective view of the valve means showing the circular collar, the cap, the valve turret and the valve function indicator.

FIG. 5 of the drawings is a top plane view of the valve means showing the valve indicator, the inlet nipple and the vent nipple.

FIG. 6 of the drawings shows partial top plane view of the bellows container and a horizontal cross-section of the valve means taken through line 6—6 of FIG. 3. FIG. 6 also includes an adaptor for a non-reflux valve which is attached to the inlet nipple and which is also shown in cross-section.

FIG. 7 of the drawings is an enlarged, detailed partial cross-section of the bellows container neck showing the upper positioning means of the hinged spider device of the valve assist means.

DETAILED DESCRIPTION OF THE DRAWINGS

Figure 8:
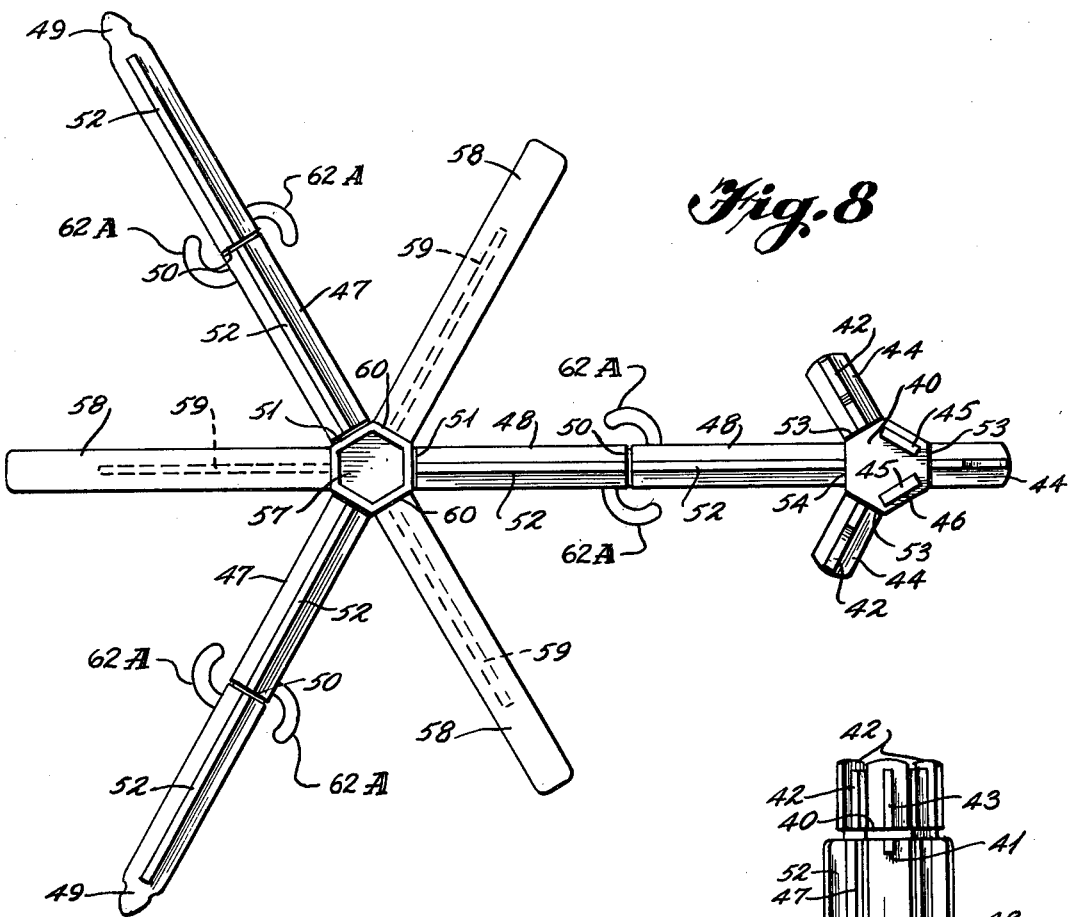
FIG. 8 of the drawings is a top plane view of the hinged spider device flattened out in the form in which it is molded and showing in dotted lines reinforcing members of the positioning legs, and also illustrating a particular locating means which may be molded therewith for retaining the elastic member.

The closed wound suction evacuator system is illustrated in FIGS. 1 and 2 showing the bellows container 1 in the expanded normal rest position with the valve means 10 and valve indicator 19 in the activate position. FIG. 3 shows the bellows container 1 and the vacuum assist means 39 in the compressed position. The bellows container 1 comprises bottom portion 5, top portion 4 and dome portion 3, and accordion-like bellow folds consisting of ridges 6 and valleys 9. The bellows container is advantageously made of resilient elastomeric material having high elastic recovery characteristics, such as polyethylene or other appropriate material. Markings, not shown, may be formed on the sidewall or bottom portion of the bellows container to permit measurement of the volume of the liquid content. The elastic memory of the plastic material from which the bellows container is made is such that in the normal rest position it is in the shape shown in FIGS. 1 and 2 of the drawings. The top portion 4, the dome portion 3 and the bottom portion 5 are much thicker in comparison to the side bellows folds 6 and 9. The side bellows folds 6 and 9 are thinner to allow the container to be compressed and expanded. The thickened top and bottom portions act to restrain the internal vacuum assist means 39 so it can be firmly located inside without the possibility of protruding through the surface which could happen if the top and bottom were too thin. The thickened top and bottom portions 3, 4 and 5 thus act as pressure plates to distribute the force applied against the top and bottom surfaces.

The top portion 4 of the bottle is extended inwardly to form dome 3 and reduce diameter neck 2 provided with external threads 7. As shown in FIG. 4, the cap 12 is constructed with top 13 and depending rim 14 with internal threads 16 which mate with the external threads 7 of the neck 2 of the bellows container 1 for threaded attachment of the cap 12 to neck 2 of the bellows container 1. The cap 12 has circular opening 15 through which there is extended upwardly the valve turret upper portion 26 while the lower valve turret portion 27 telescopically fits within the neck 2 of the bellows container 1. The valve turret 11 about midway between the upper turret portion 26 and the lower turret portion 27 has fixedly connected thereto a horizontal circular flange 31. Immediately above the horizontal circular flange 31, there is disposed an annular stop and sealing means 32. The upper valve turret portion 26 contains therein wall suction orifice or vent orifice 29 and patient or inlet orifice 28. The vent orifice 29 and inlet orifice 28 are disposed at an angular distance apart of about 140°. The circular collar 17 of the valve means telescopically, slidingly and sealingly fits over the valve turret upper portion 26 to form a valve sealing means. The lower portion of circular collar 17 abuts and forms a tight fit with annular stop and seal means 32. The upper portion of collar 17 snaps and locks into place under circular bead retaining means 33 which surrounds the periphery of the top of valve turret upper portion 26. The circular bead retaining means 33 serves to snap collar 17 downwardly in place while at the same time sealing the top portion of circular collar 17.

The circular collar 17 is sealingly and slidingly fitted to the upper valve turret portion 26 to form a tight seal valve means and allow rotation of collar 17 about and around the valve turret upper portion 26. The circular collar 17 contains integral therewith hollow inlet nipple 18 having on the top thereof valve indicator 19 for selectively positioning the circular collar 17 on the valve turret upper portion 26. Inlet nipple 18 contains inlet tube retaining means 20 which forms a tight sealing fit with an inlet or drainage plastic tube not shown. The interior of the bellows container and of circular ring 17 communicate with the drainage tube (not shown) through orifice 21 in the inlet nipple 18. The circular collar 17 also has integrally therewith hollow vent nipple 22 having tube retaining means 23. The interior of the bellows container and of circular collar 17 communicate with the vent outlet tube (not shown) through orifice 24 in the vent nipple 22.

The valve means 10 is assembled on the bellows container 1 by first telescopically fitting the valve turret lower portion 27 into the opening 8 of neck 2 of the bellows container 1. The cap 12 is then screwed onto the neck 2 by the internal threads 16 of the cap and mating external threads 7 of the neck 2 to form a tight sealing fit with the neck 2 of bellows container 1. The circular collar 17 is then telescopically fitted over the valve turret upper portion 26 and snapped in place over circular retaining means 33. The top surface of the valve turret upper portion 26 is suitably printed or marked to make function indicator 30 which shows the positions to which valve indicator 19 may be pointed to carry out the various functions of the valve means.

The vacuum assist means 39 is inserted into the bellows container 1 prior to attaching the valve means 10 to the bellows container 1. The vacuum assist means 39 include a hinged plastic spider device and elastomeric ring 61 which acts as the mechanical force means. The spider device includes two or more rib member means, such as rib members 47 and 48, disposed between the top portion 4 and the bottom portion 5 of the evacuator. The vacuum assist means further includes a positioning means to securely locate the rib member means within the container. The top portion of the vacuum assist means is held in position in the neck 2 and dome 3 of bellows container 1 by arm positioning members 42. Arm positioning member 42 is integrally connected to arm member 44 which is hingedly connected to top plate 40 by hinge means 53. The arm member 44 is strengthened by arm reinforcing members 43. The top plate 40 is strengthened by top plate reinforcing members 41.

Integrally connected to the top portion of top plate 41 are connecting and locking means 45 having an opening 46 through which bayonette members 49 of first and second rib members 47 are inserted and locked into place. In the embodiment shown in FIG. 2 of the drawings, the first and second rib members 47 connect top plate 40 to bottom plate 57. The first and second rib members 47 have an upper portion which are hingedly connected by hinge means 50 to a lower portion at a point about midway between the rib members. There is a third rib member 48, also connecting the top plate 40 to bottom plate 57. The third rib member 48 also has a hinge means 50 about midway between its upper portion and lower portion. About midway between the rib members 47 and rib member 48 approximate to the hinge means 50, there is an elastomeric ring 61 which is held in place by elastic ring positioning means 62 which holds the elastic ring 61 operably in position. The lower portion of the rib members 47 and 48 are hingedly connected to bottom plate 57 by hinge means 51. The hinge means 53 of the arm members 42, the hinge means 54 of the upper plate 40, the hinge means 50 of the rib members 47 and 48, and the hinge means 51 of the lower plate 57 are formed from a flexible portion of the material from which the hinged plastic spider device is molded.

The lower portion of the hinged plastic spider device is held in position in the bellows container 1 by leg positioning members 58. The leg positioning members 58 are reinforced by leg reinforcing members 59.

Figure 14:
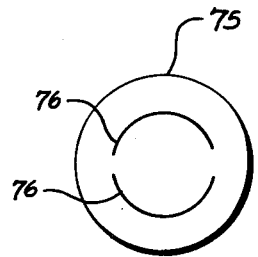
FIG. 14 of the drawings is a top view of a non-reflux valve which is also shown in position in FIG. 6.

The valve means 10 is further described with reference to FIGS. 4, 5 and 6 of the drawings. The valve means 10 comprises valve turret 11 consisting of valve turret upper portion 26 and valve turret lower portion 27. About midway between the upper and lower portion of valve turret 11, there is disposed horizontal circular flange 31. Immediately above flange 31 is annular stop and seal means 32. The valve turret upper portion 26 contains vent orifice 29 and inlet orifice 28. The top of valve turret upper portion 26 contains circular bead retaining means 33. The valve cap 12 fits over upper portion 26 of the turret 11 and when threaded onto neck 2 of bellows container 1 tightly seals horizontal circular flange 31 to the top portion of neck 2 of bellows container 1 by the action of internal threads 16 on cap 12 and external threads 7 on neck 2 of the bellows container 1. The circular collar 17 telescopically fits over the valve turret upper portion 26 to slidingly and sealingly form the operational part of the valve means 10. The lower portion of circular collar 17 is sealed against annular stop and seal means 32 and the upper portion of circular collar 17 is snapped over circular retaining means 33 held in place and sealed by circular retaining means 33. The circular collar 17 has integrally connected thereto hollow inlet nipple 18 having on the top thereof valve indicator 19. The inlet nipple 18 has at the outer portion thereof inlet tube retaining means 20 by which a drainage tube, not shown, may be sealingly connected to the inlet nipple 18. Communication between the interior of bellows container 1 and of the drainage tube (not shown) is provided by orifice inlet 21 of nipple 18 and inlet orifice 28 of upper turret portion 26. The inlet nipple 18 may also be provided with an adaptor 77 as shown in FIG. 6. The adaptor 77 allows a non-reflux valve 78 to be positioned to cover the orifice inlet 21. The non-reflux valve 78 is also shown in FIG. 14. The valve 78 is preferably made of natural latex rubber and is only 0.010 inches thick. The valve 78 has two curved die cuts 76. The valve 78 is a variation of a leaf valve. The valve 78 acts to prevent retrograde flow of fluid. The adaptor 77 may be made of vinyl, and if used, is preferably bonded to the inlet nipple 18 to become a rigid attachment. The adaptor 77 locates the valve 78 between the orifice inlet 21 of the inlet nipple 18 and the collar 80 of the adaptor 77. The collar 80 provides a decreased diameter in the bore 81 to allow the valve 78 to be held in place. The bore 81 runs through the adaptor 77 to provide communication between the tubing (not shown) and the inlet orifice 28. If the adaptor is used, the tubing (not shown) may be sealingly connected to the adaptor 77. The circular collar 17 has disposed clockwise at an angular distance of about 140° from nipple 18 hollow vent nipple 22 having vent tube retaining means 23 thereon. A vent tube or a wall suction tube (not shown) may be sealingly connected to vent or outlet nipple 22 by vent tube retaining means 23. Communication between the interior of bellows container 1 and of a vent tube or wall suction tube is provided by orifice outlet 24 in hollow vent nipple 22 and vent orifice 29.

The top of valve turret means 11 is provided with function indicator 30. The function indicator 30 may have printed or otherwise marked thereon a V over vent orifice 29, a P over inlet orifice 28. The P or patient position is angularly spaced about 140° clockwise from the V or wall suction position. An A or activate position is angularly spaced about 80° clockwise from the P or patient position. Accordingly, the V position is angularly spaced about 140° clockwise from the A position. A H or hold position is spaced about midway between the P and A positions. It is understood that the angular spacing in the valve means 10 may be set up differently as long as the position alignment described in the following two paragraphs is achieved.

As illustrated in FIG. 4 of the drawings when valve indicator 19 is aligned with the wall suction position V, and hence aligned with vent orifice 29, inlet nipple 18 is aligned with vent orifice 29 and vent nipple 22 is aligned with inlet orifice 28. In this position, a wall suction tube (not shown) attached to vent nipple 22 can draw a suction on the interior of an evacuator container and a drainage tube (not shown) attached to inlet nipple 18, thereby providing suction to a closed wound. As previously stated, when it is desirable to use wall suction, it is more desirable to use a rigid container than a collapsible container such as the bellows container 1. With the wall suction adaption means built in to the removable valve 10, this allows the complete valve means 10 with tubing (not shown) to be transferred to an appropriate rigid container without disturbing the patient. If the wall suction is used directly on the bellows container 1, it will cause the bellows to collapse. Therefore, not as much fluid is capable of being collected.

When the circular collar 17 is positioned as shown in FIG. 1 with valve indicator 19 aligned with activate position A of function indicator 30, the bellows container 1 can be collapsed as shown in FIG. 3 and air in the bellows container vented through vent orifice 29 and vent nipple 22. When the valve indicator 19 is aligned with the hold H position, both the vent orifice 29 and the inlet orifice 28 are sealed by circular collar 17 and the bellows container 1 can be maintained in the active position compressed as shown in FIG. 3. When it is desired to use the independently operable closed wound suction evacuator system, a drainage tube (not shown) is attached to inlet nipple 18 and the valve indicator 19 aligned with the patient P position on the function indicator 30, i.e. with the inlet orifice 28. The collar 17, when the valve indicator 19 is in the P position, seals vent orifice 29 such that a suction is applied to the drainage tube as the bellows container 1 returns to its expanded normal rest position. FIG. 6 illustrates two O-rings 79, one which is provided to seal off the inlet orifice 28 and one to seal off the vent orifice 29 from the atmosphere.

The vacuum assist means 39 is described in more detail with reference to FIGS. 7, 8, 9 and 10 of the drawings which also illustrate a convenient method of manufacture and assembly of the vacuum assist means.

The FIG. 7 of the drawings is an enlarged detailed partial cross-section of the bellows container 1, neck 2 and the upper arm positioning members 42 of the hinged spider device of the valve assist means 39.

The FIG. 8 shows a top plane view of the single-piece hinged plastic spider device in the manner that it is laid out as formed by molding in a single piece. The hinged plastic spider device is preferably formed from elastomeric polypropylene in a manner such that it has flexible hinge means 53 connecting arm members 44 to top plate 40, flexible hinge means 54 connecting rib member 48 to top plate 40, flexible hinge means 50 positioned about midway between rib members 47 and 48, flexible hinge means 56 connecting the bottom of rib members 47 and 48 with the bottom plate 57, and flexible hinge means 60 connecting leg positioning members 58 to bottom plate 57. The upper arm positioning means comprises top plate 40 to which there is hingedly connected arm members 44 and arm positioning members 42. The arm members 44 contain on their lower surface arm reinforcing members 43. The lower surface of top plate 40 have top plate reinforcing members 41. The first and second rib members 47 have at their extreme end bayonette members 49 which are hinged to the upper portion of the rib members 47. The bayonette members 49 fit through and lock into openings 46 of connecting and locking means 45. The bayonette members 49 are then sealed to the top plate 40. The connecting and locking means 45 are integrally connected to the top plate 40 (see also FIG. 7). The third rib member 48 connects the top plate 40 to the bottom plate 57. The first and second rib members 47 when connected by bayonette member 49 to connecting and locking means 45 serve to connect the top plate 40 to the bottom plate 57. The first and second rib members 47 and third rib member 48 have rib reinforcing members 52. The bottom portion of the hinged plastic spider device is held in place in the bellows container 1 by leg positioning members 58 which are hingedly connected by hinge means 60 to bottom plate 57. The leg positioning members 58 have leg reinforcing members 59.

Figure 9:
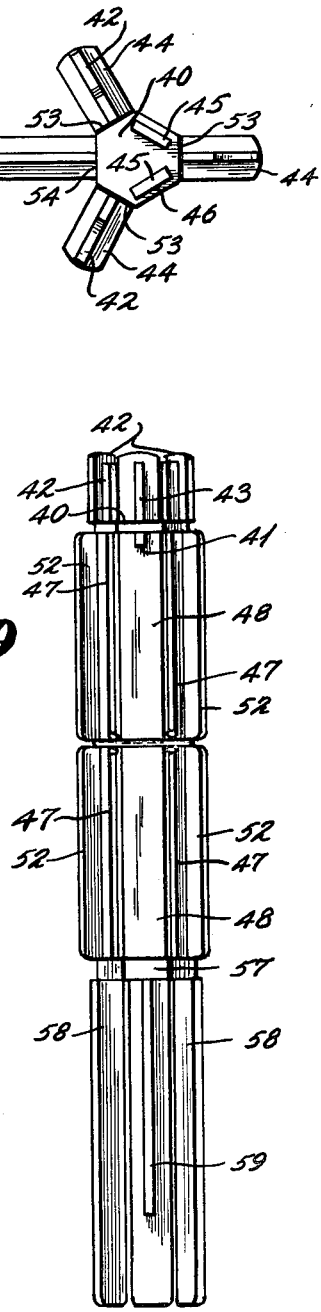
FIG. 9 of the drawings shows the hinged spider device of the vacuum assist means assembled and positioned for inserting into the bellows container.
Figure 10:
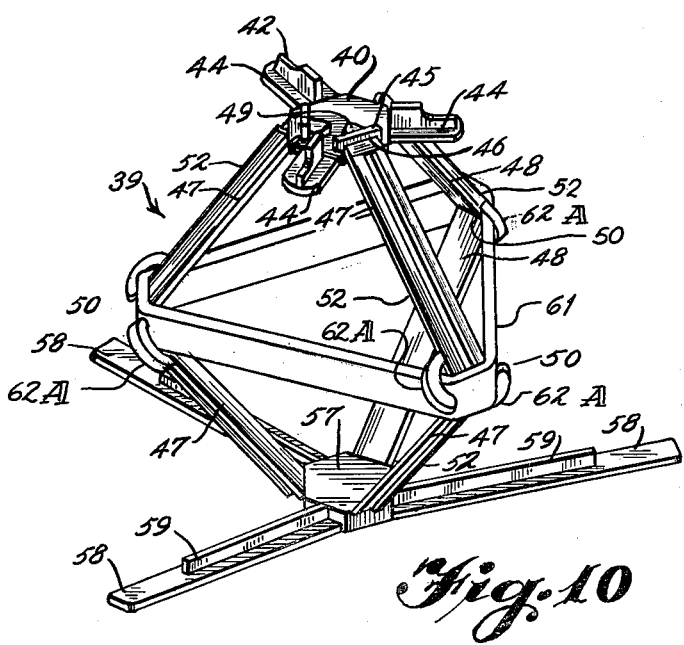
FIG. 10 of the drawings shows a perspective view of the vacuum assist means of FIG. 8 in a partially compressed shape.
Figure 13:
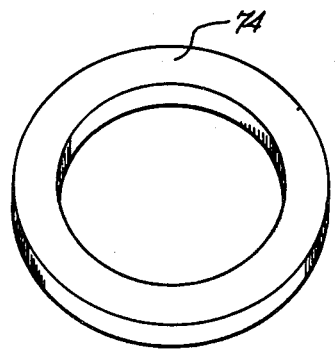
FIG. 13 of the drawings is a perspective view of the elastic member of the preferred embodiment which is also shown in FIG. 10.

The hinged plastic spider device after being formed by molding is laid out as illustrated in FIG. 8. The first and second rib members 47 are then connected to the top plate 40 as previously discussed. The arm members 44 are extended by hinge means 53 vertically upward and the leg positioning members 58 are extended by the hinge means 60 vertically downward and the rib members 47 and 48 are positioned so that they form an essentially vertical straight line as shown in FIG. 9. Prior to inserting the hinged plastic spider device into the bellows container 1, the elastomeric ring 61 must be placed around the rib members 47 and 48. The elastomeric ring 61 is retained in position by elastomeric ring positioning members 62 as shown in FIGS. 2, 3, 8, 9 and 10, although the preferred configuration of the elastomeric ring positioning means 62A is shown in FIGS. 8 and 10. The preferred positioning means 62A includes a pair of curved members, 62A on each rib members 47 and 48 located near the hinge means 50. One portion of the pair of curved members protrudes from one side of the upper portion of each rib member 47 and 48 and is curved downward and the other portion protrudes from the opposite side of the lower portion of each rib member 47 and 48 and is curved upward. The elastomeric ring 61 is held in place by these positioning members 62A as shown in FIG. 10. The preferred embodiment of the elastic ring is shown in FIGS. 10 and 13, and is preferably made of natural rubber. The hinge plastic spider device is then inserted through the opening 8 in the neck 2 of bellows container 1, the leg positioning members 58 extended outwardly in the bottom of the bellows container 1 and the arm members 42 extended outwardly to position the hinged plastic spider device within the bellows container 1 as shown in FIGS. 10 and 2 and 3 of the drawings.

After positioning the vacuum assist means 39 in the bellows container 1, the valve means 10 is assembled onto the bellows container 1 in the manner previously described above.

It is understood that the spider device may be made with two or more positioning arm members, two or more rib members and two or more positioning leg members. The preferred embodiment of the invention utilizes three arm members, three rib members and three leg members. In an embodiment where four rib members are used, either one or two bayonette connecting means may be used, depending on how the spider device is molded. The rib members, as before, alternate with the positioning leg members and the positioning arm members. Alternate configurations for the spider device will be discussed further on.

OPERATION OF THE PREFERRED EMBODIMENT

A preferred embodiment of the invention is described with reference to FIGS. 1 to 6 of the drawings.

The closed wound evacuator system, as illustrated in FIGS. 1 and 2 of the drawings, comprises a bellows container 1 inside of which is positioned a vacuum assist means 39 and on top of which is a valve means 10 retained by a screw on cap 13.

The bellows container 1 is shown in its normal at rest position (FIGS. 1 and 2) and the vacuum assist means 39 is shown in its normal expanded shape (FIG. 2). The valve indicator 19 on inlet nipple 18 is shown (FIGS. 1 and 2) aligned with the activate position A on the function indicator 30. In this position, inlet orifice 28 is sealed by circular collar 17 and vent nipple 22 is aligned with vent orifice 29. As downward pressure is applied to the top of the bellows container 1 to axially compress downwardly the top 4 towards the bottom 5 of the bellows container 1, air in the bellows container is expelled and vented to the atmosphere through vent orifice 29 and vent nipple 22 to activate the suction evacuator system. The downward compression of the bellows container 1 also compresses downwardly the hinged plastic spider device of the vacuum assist means 39 (FIG. 3). After compression of the bellows container 1 and the hinged plastic spider device to the activated position, the valve indicator 19 on inlet nipple 18 of the valve means 10 is rotated to align the valve indicator 19 with the hold position H on the function indicator 30 (see FIGS. 5 and 6). Aligning the valve indicator 19 with the hold position H causes the inner surface of circular collar 17 to close off and seal both inlet orifice 28 and vent orifice 29 of the valve turret upper portion 26, and allows the suction evacuator system to be maintained in the hold, activated position until ready for use.

After activation of the suction evacuator system, as part of a post-operative procedure, a drainage tube (not shown) is inserted into a surgical wound and the wound closed. The drainage tube is then slidingly connected to inlet nipple 18 and forms a tight sealing fit with the inlet tube retaining means 20. The valve indicator 19 is then aligned with the patient position P on function indicator 30 which aligns inlet nipple 18 with the inlet orifice 28. The inner surface of the circular collar 17 closes off and seals vent orifice 29. Upon release of the manual compressing force and/or merely by turning the valve indicator 19 to the patient position P, the resiliency of the corrugated bellows sidewalls of bellows container 1 and the force applied by the stretched circular elastomeric ring 61 of the hinged spider device of the vacuum assist means 39 act in combination, i.e. coact to expand the bellows container 1 to its normal rest position and to expand the hinged plastic spider device of the vacuum assist means 39 to its normal expanded shape. This coaction develops a negative pressure within the bellows container 1 which in turn develops a suction transmitted through the drainage tube (not shown) to the closed wound to drain from the wound whatever fluid may have been collected in the wound. The fluid is drained through the hollow drainage tube and collected in the bellows container 1. Because the wound is closed, air does not enter into the drainage tube and/or the bellows container to disturb the operation of the bellows container and as the bellows container continues to expand slowly, it fills with drained fluid. While this takes place, the evacuation system may be attached on or positioned adjacent to the patient by suitable means. In operation, as the bellows container is expanded and the vacuum developed by the bellows container decreases with the outward movement, the vacuum developed by the vacuum assist means increases with the outward movement of the hinged plastic spider device of the vacuum assist means. The net result is a constant relatively level amount of vacuum being developed during the useful draw of the bellows container and applied to the fluids in the closed wound.

If for any reason suction is broken and the bellows container expands without drawing fluid into its interior, the suction can be reestablished merely by moving the valve indicator 19 to the activate position A, compressing the bellows container to vent air to the atmosphere and to then turn the valve indicator to the patient position P. As before, the expansion of the bellows container and the expansion of the vacuum assist means will develop a negative pressure in the bellows container and a suction in the drainage tube. When the bellows container is filled, the valve should be moved to the hold H position to close off the wound from either the inlet orifice 28 or the vent orifice 29 and then the valve means with wound tubing still attached, can be detached from the container and disposed of as desired. A new unit may then be attached to the drainage tube and the operation repeated until further drainage of the patient's wound is unnecessary. This allows the container to be emptied or changed without disturbing the patient and without directly exposing the wound to the atmosphere since the still connected tubing is blocked off from direct contact with the atmosphere by the valve means being in the hold H position.

ALTERNATE EMBODIMENTS

It is understood that this invention may have numerous embodiments, varying certain features without departing from the scope of the invention.

For example, the spider device does not have to be manufactured from plastic and it also does not have to be manufactured in one piece. Any suitable material such as light weight metal may be used for the rib members of the spider device. Two or more rib members may be used in the spider device. These rib members may be located in the device by any convenient means and not necessarily by arm positioning members and leg positioning members. For example, the bottom plate 57 of the spider device could be located over a protruding stud on the bottom portion of the evacuator. Any other conventional locating or fastening means can be used to hingedly connect the rib members to the top and bottom portions of the evacuator. Also, any convenient hinge means can be used to connect the top portion of the ribs to the bottom portion of the ribs. The hinges do not have to be integral with the ribs as in the molded embodiment of the spider device. The molded single piece spider device is a unique and convenient way of manufacturing the spider device in one simple piece.

The elastic ring positioning and locating members on the ribs also may utilize any convenient positioning means to retain the elastic ring in place about the hinged ribs. In fact in the Summary of the Invention, as previously mentioned, it is even possible to use springs as a mechanical force means to connect the ribs such that as the spider device is compressed it causes the springs to expand or stretch. When the downward restraint is released, the springs apply a force which act to return the spider device to its normal expanded shape.

The mechanical vacuum assist device may also be used in any evacuator device having a supporting top and bottom with compressible sides in between, and not just in bellows-type evacuators. The purpose of the spider device is to assist in creating a relatively constant vacuum level while drawing fluids from a closed wound. For example, a spider device may be incorporated into the style of evacuators shown in U.S. Pat. No. 3,115,138. The devices described in U.S. Pat. No. 3,115,138 which include springs fixedly engaged between a top and bottom of the enclosed evacuator and having compressible sides may utilize a spider assist device.

When the evacuator is compressed, the springs are compressed. When the compressive pressure is released, the springs act to expand the evacuator. Much like the bellows container, this type of spring device experiences a rapid decrease from maximum negative pressure to a minimum negative pressure during the expansion of the container from the compressed to normal position. If a spider assist device is utilized in this type of evacuator, when the evacuator and spider assist device are compressed, upon release of the compressive force, initially only a small amount of force is being applied by the vacuum assist device to push the container back to its normal rest position, but as the evacuator container moves toward its normal rest position, an increasingly greater force is applied by the vacuum assist or spider assist means to expand the container, and hence an increase in the amount of vacuum developed by the spider device as it returns to its expanded condition. The net result in combination with the spring mechanism, is a relative level amount of vacuum developed during the useful draw of the container.

If the overall force created from start to finish of the spider device is viewed, the force when a vacuum assist means is compressed is minimal and begins to increase as the spider device expands. The force then levels off and then drops back to zero when the device is fully back to rest position.

Since the spider device can be designed to create a linear force, it therefore can have a linear stroke. It is possible to use the spider device as the sole means of expanding a compressible evacuator (i.e. no bellows mechanism is used and no springs fixedly attached between the top and bottom of the compressible container are used), and still obtain a relative level amount of vacuum. The container can be made so that only the middle or center portion of the stroke of the spider device is used. For example, if a spider device is capable of being compressed 6 inches from its fully expanded state to its fully compressed state, it is possible to utilize this device in an evacuator sized to prevent the device from being fully expanded or fully compressed. Hence, only the center of the stroke is used. In this way, it is still possible to obtain a relative level amount of vacuum during the useful draw of the evacuator which is the desired objective, and the main purpose in using the spider vacuum assist mechanism.

In the bellows device, described in the preferred embodiment, it was stated that the top and bottom portions of the evacuator should be thicker than the sides to act as a pressure plate. In the bellows device the pressure plate is integrally incorporated in the plastic evacuator. It is also possible to have the pressure plates separate from the actual container, but located within the container against the top and bottom portion, which is done in some currently available compressible evacuators.

Figure 11:
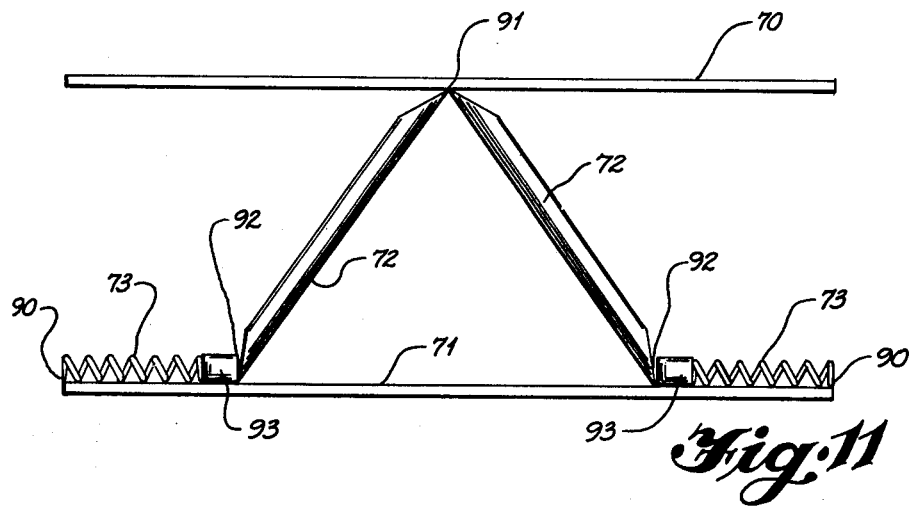
FIG. 11 of the drawings is a side view of an alternate embodiment for a vacuum assist means in the unactivated state.
Figure 12:
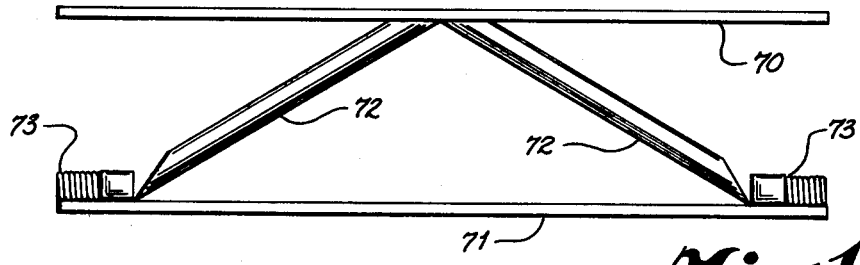
FIG. 12 of the drawings is a side view of the vacuum assist means of FIG. 11 in the activated or compressed state.

A further modified embodiment of the spider assist device is illustrated in FIGS. 11 and 12. The device is shown located between the top and bottom pressure plates 70 and 71, but is not shown within an evacuator.

FIG. 11 illustrates the device in the expanded or rest condition. Although the device may be made with two or more rib members, the embodiment shown consists of 2 rib members 72 which are hingedly attached to the top pressure plate 70 at hinge means 91. The bottom of the ribs 72 are each hingedly attached by a hinge means 92 to a pusher means 93 which is located against an end of a longitudinal spring 73. The springs 73 are located on the bottom pressure plate 71, and each retained longitudinally in a spring retaining means 90. When the spider device is positioned in a compressible evacuator and the evacuator and spider device are compressed or activated, the springs 73 are also compressed. Upon release from this position, this embodiment of the spider device acts in the same manner as the previously described spider devices by the springs 73 pushing inwardly at the hinge means 92 to create a linear force which initially is minimal and begins to increase as the spider device expands. It therefore can be used in the same manner as the previously described spider assist devices for assisting in creating a relative level amount of vacuum in a compressible evacuator.

The improved closed wound suction evacuator system of the present invention develops a constant nearly level vacuum during the useful draw cycle of the bellows container. It also allows the system to be stored in the activated state until ready for use, is easy to operate, is small and light-weight and can be easily attached to a patient.

While this invention has been described in terms of its preferred embodiment and various modifications, those skilled in the art can appreciate that other modifications can be made without departing from the spirit and scope of this invention.

We claim:

1. A medical evacuator system for evacuating fluids from the body comprising in combination:
   (a) a closed compressible container having top and bottom portions connected by a flexible sidewall, said container adapted to be compressed and to expand to develop a vacuum on expansion;
   (b) a vacuum assist means disposed within said container which assists in the expansion of the container and in developing the vacuum in the container; and (c) an outlet means providing communication between the interior of the container and the atmosphere and an inlet means providing communication between the interior of the container and a drainage tube, said vacuum assist means comprised of a spider device having two or more rib member means disposed between the top and bottom portions, a positioning means to securely locate the rib member means within the container, a hinge means to allow the rib member means to move from an extended rest position to a compressed activated position and a separate mechanical force means engaging exteriorly on said rib member means which mechanical force means acts in a direction substantially perpendicular to said flexible sidewall to return the rib member means to their extended rest position.

2. The evacuator system of claim 1, wherein said compressible container is a bellows container and wherein said flexible side walls connecting the top and bottom portions are accordion like and are made of a resilient elastomeric material, and are comprised of continuous alternate ridges and valleys adapted to be compressed and to expand to develop a vacuum on expansion.

3. The evacuator system of claim 2, wherein said bellows container top portion is extended inwardly to form a reduced diameter neck provided with external threads and an opening communicating with the interior of said container.

4. The evacuator system of claim 2, wherein said top and bottom portions are substantially thicker than the compressible side wall of the container to provide substantially rigid top and bottom portions in comparison to the flexible side walls.

5. The evacuator system of claim 1, wherein said compressible container further includes a plurality of springs disposed between the top and bottom of the container, with the opposite ends of each spring engaging the top and bottom, respectively, to exert a separating force thereon, and wherein the springs within the container are adapted to be compressed and to develop a vacuum on expansion.

6. The vacuum assist means of claim 1, wherein said positioning means is attached to the rib member means and comprises upper positioning members and lower positioning members and wherein the rib member means connect the upper positioning members and the lower positioning members and wherein said rib member means have the mechanical force means disposed about the middle portion of said rib member means.

7. The vacuum assist means of claim 6, wherein the compressible evacuator container has a reduced neck in the top thereof, said neck having an opening communicating with the interior of said container and wherein the upper positioning members of the vacuum assist means cooperate with the opening in the neck at the top of the compressible container to maintain the position of the vacuum assist means at about the center of the neck opening and the lower positioning members maintain the position of the valve assist means in about the center of the bottom of the container.

8. The vacuum assist means of claim 6 wherein said rib member means are hingedly connected to said upper positioning members, and wherein said rib member means are hingedly connected at a point about midway between the upper portion of said rib member means and a lower portion of said rib member means, said mid-point hinge means of said rib member means being capable on downward compression of said rib member means of flexing outwardly, the outward flexing of said rib member means begin restrained by the mechanical force means disposed around said rib member means at a point approximate to said mid-point hinge means, and the lower portion of said rib member means being hingedly connected to said lower positioning members.

9. The vacuum assist means of claim 1, wherein the positioning means hingedly connects the top of the rib member means to the top portion of the evacuator and wherein the mechanical force means is comprised of a plurality of springs which are disposed lengthwise along the bottom portion of the evacuator and wherein said springs are longitudinally contained in a retaining means and wherein each spring is attached to a corresponding pusher means located against the end of the spring and wherein said pusher means are hingedly attached to the bottom of corresponding rib member means and whereas compression of the evacuator and spider device results in compression of the springs, and upon release of the compressive force, the springs expand outwardly back to their rest position resulting in an upward linear force which assists in returning the evacuator to its extended rest position.

10. An evacuator system for evacuating fluids from the body comprising in combination:
(a) a compressible container having top and bottom portions connected by a flexible sidewall, said container adapted to be compressed and to expand to develop a vacuum on expansion;
(b) a vacuum assist means disposed within said container which assists in the expansion of the container and in developing the vacuum in the container; and
(c) an outlet means providing communication between the interior of the container and the atmosphere and an inlet means providing communication between the interior of the container and a drainage tube, said vacuum assist means comprised of a spider device including two or more rib member means disposed between the top and bottom portions, a positioning means to firmly locate the rib member means within the container, a hinge means to allow the rib member means to move from an extended rest position to a compressed activated position and a mechanical force means which acts to return the rib member means to their extended rest position, said positioning means being attached to the rib member means and comprising an upper positioning means and a lower positioning means, wherein said upper positioning means includes upper positioning members and a top plate member connected thereto, and wherein said lower positioning means includes lower positioning members and a bottom plate member connected thereto, and wherein the rib member means connects the upper positioning means and the lower positioning means and wherein said rib member means have the mechanical force means disposed about the middle portion of said rib member means, and wherein the upper positioning members are arms hingedly connected to the top plate member and the upper portion of said rib member means are hingedly connected to said top plate member, and wherein said rib member means are hingedly connected at a point about midway between the upper portion of said rib member means and a lower portion of said rib member means, said mid-point hinge means of said rib member means being capable on downward compression of said rib member means of flexing outwardly, the outward flexing of said rib member means being restrained by the mechanical force means disposed around said rib member means at a point approximate to said mid-point hinge means, and wherein the lower portion of said rib member means are hingedly connected to the bottom plate member, and wherein the lower positioning members are legs hingedly connected to said bottom plate member.

11. The evacutor system of claim 10, wherein said compressible container is a bellows container and wherein said flexible side walls connecting the top and bottom portions are accordion like and are made of a resilient elastomeric material, and are comprised of continuous alternate ridges and valleys adapted to be compressed and to expand to develop a vacuum on expansion.

12. The evacuator system of claim 10, wherein said compressible container further includes a plurality of springs disposed between the top and bottom of the container, with the opposite ends of each spring engaging the top and bottom, respectively, to exert a separating force thereon, and wherein the springs within the container are adapted to be compressed and to develop a vacuum on expansion.

13. The vacuum assist means of claim 10, wherein the vacuum assist means is plastic.

14. The vacuum assist means of claim 10, wherein the mechanical force means is a substantially circular elastomeric ring.

15. The vacuum assist means of claim 10, wherein the mechanical force means is comprised of springs connecting the rib members.

* * * * *